United States Patent [19]

Imai

[11] Patent Number: 4,578,107

[45] Date of Patent: Mar. 25, 1986

[54] HERBICIDAL IMIDAZOLIDINE-2-ONE DERIVATIVES

[75] Inventor: Tetsuya Imai, Naruto, Japan

[73] Assignee: Otsuka Kagaku Kabushiki Kaisha, Osaka, Japan

[21] Appl. No.: 619,149

[22] PCT Filed: Sep. 27, 1983

[86] PCT No.: PCT/JP83/00318

§ 371 Date: May 25, 1984

§ 102(e) Date: May 25, 1984

[87] PCT Pub. No.: WO84/01383

PCT Pub. Date: Apr. 12, 1984

[30] Foreign Application Priority Data

Sep. 27, 1982 [JP] Japan .................. 57-169207
Sep. 30, 1982 [JP] Japan .................. 57-171311
Feb. 18, 1983 [JP] Japan .................. 58-26592

[51] Int. Cl.$^4$ .................. A01N 43/50; C07D 233/40
[52] U.S. Cl. .................. 71/92; 548/319
[58] Field of Search .................. 548/319; 71/92

[56] References Cited

U.S. PATENT DOCUMENTS

| | | | |
|---|---|---|---|
| 3,304,312 | 2/1967 | Beachem | 548/319 |
| 4,285,690 | 8/1981 | North | 548/319 X |
| 4,306,872 | 12/1981 | Herbes et al. | 548/319 X |
| 4,345,936 | 8/1982 | Thibault et al. | 548/319 X |

FOREIGN PATENT DOCUMENTS

| | | | |
|---|---|---|---|
| 47-5840 | 2/1972 | Japan | 548/320 |
| 50-11452 | 5/1975 | Japan | 548/320 |
| 58-148863 | 9/1983 | Japan | 548/320 |

OTHER PUBLICATIONS

March, J., *Advanced Organic Chemistry*, McGraw Hill, New York, 1968, pp. 663 and 678-679.
Streitwieser, A. et al., *Introduction to Organic Chemistry*, MacMillan, New York, 1976, p. 1209.

Primary Examiner—Richard A. Schwartz
Attorney, Agent, or Firm—Armstrong, Nikaido, Marmelstein & Kubovcik

[57] ABSTRACT

An imidazolidine-2-one derivative represented by the formula

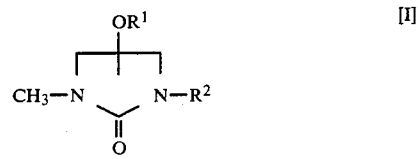

wherein $R^1$ represents hydrogen atom, lower alkyl group, lower alkoxy lower alkyl group, benzyl group, lower alkoxycarbonyl lower alkyl group or lower alkylcarbamoyloxy group and $R^2$ represents a group —Ar or group —CONH—Ar wherein Ar represents a phenyl group, phenoxyphenyl group or aralkyloxyphenyl group each of which may be substituted with a halogen atom, nitro group, lower alkyl group, lower alkoxy group or haloalkyl group, a process for preparing the same and a herbicidal composition containing the same.

12 Claims, No Drawings

HERBICIDAL IMIDAZOLIDINE-2-ONE DERIVATIVES

TECHNICAL FIELD AND DISCLOSURE OF INVENTION

This invention relates to novel imidazolidine-2-one derivatives, to processes for preparing the derivative and to herbicides containing the derivative as their active component.

The imidazolidine-2-one derivatives of the present invention are novel compounds undisclosed in literature and represented by the formula [I].

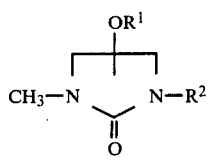

wherein $R^1$ represents hydrogen atom, lower alkyl group, lower alkoxy lower alkyl group, benzyl group, lower alkoxycarbonyl lower alkyl group or lower alkylcarbamoyloxy group and $R^2$ represents a group —Ar or group —CONH—Ar wherein Ar represents a phenyl group, phenoxyphenyl group or aralkyloxyphenyl group each of which may be substituted with a halogen atom, nitro group, lower alkyl group, lower alkoxy group or haloalkyl group.

Particularly preferred compounds of the present invention represented by the formula [I] are as follows:

compounds represented by the formula

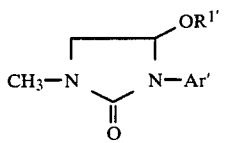

wherein $R^{1'}$ represents hydrogen atom, lower alkyl group, lower alkoxy lower alkyl group, benzyl group or lower alkoxycarbonyl lower alkyl group and Ar' represents a phenyl group, phenoxyphenyl group or aralkyloxyphenyl group each of which may be substituted with a halogen atom, lower alkyl group, lower alkoxy group or haloalkyl group;

compounds represented by the formula

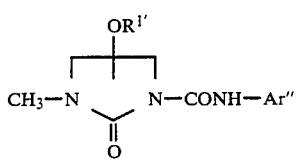

wherein $R^{1'}$ is as defined above and Ar" represents a phenyl group which may be substituted with a halogen atom, nitro group, lower alkyl group, lower alkoxy group or haloalkyl group; and compounds represented by the formula

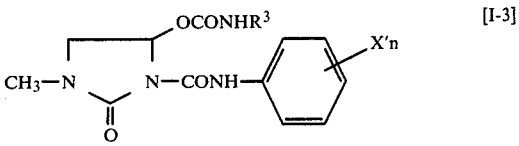

wherein $R^3$ represents a lower alkyl group, $X'$ represents hydrogen atom, halogen atom, lower alkyl group, lower alkoxy group, benzyloxy group or haloalkyl group, and n is an integer of 1 to 3.

Exemplary of the lower alkyl groups mentioned in this specification are methyl, ethyl, n-propyl, isopropyl, n-butyl, sec-butyl, isobutyl, tert-butyl, etc. Representative of the lower alkoxy lower alkyl groups are methoxymethyl, methoxyethyl, methoxypropyl, butoxymethyl, etc. Illustrative of the lower alkoxycarbonyl lower alkyl groups are methoxycarbonylmethyl, ethoxycarbonylmethyl, propyloxycarbonylmethyl, methoxycarbonylethyl, ethoxycarbonylethyl, propyloxycarbonylethyl, etc. Examplary of the lower alkylcarbamoyloxy groups are methylcarbamoyloxy, ethylcarbamoyloxy, propylcarbamoyloxy, isopropylcarbamoyloxy, etc. Representative of the aralkyloxyphenyl groups are benzyloxyphenyl, phenethyloxyphenyl, etc. Illustrative of the halogen atoms are fluorine, chlorine, bromine, iodine, etc. Exemplary of the lower alkoxy groups are methoxy, ethoxy, n-propyloxy, isopropyloxy, n-butoxy, etc. Representative of the haloalkyl groups are monochloromethyl, monochloroethyl, monochloropropyl, dichloroethyl, monobromomethyl, monobromoethyl, monobromopropyl, monofluoromethyl, trifluoromethyl, trifluoroethyl, etc. Illustrative of the phenyl groups substituted with halogen, nitro, lower alkyl, lower alkoxy or haloalkyl are 2-chlorophenyl, 3-chlorophenyl, 3,4-dichlorophenyl, 2-fluorophenyl, 2-nitrophenyl, 3-nitrophenyl, 2-methylphenyl, 3-methylphenyl, 4-methylphenyl, 3,4-dimethylphenyl, 2-isopropylphenyl, 2-methoxyphenyl, 3-methoxyphenyl, 2-n-propyloxyphenyl, 2-isopropyloxyphenyl, 3-trifluoromethylphenyl, etc. Exemplary of the phenoxyphenyl groups substituted with halogen, nitro, lower alkyl, lower alkoxy or haloalkyl are 2-chlorophenoxyphenyl, 3-chlorophenoxyphenyl, 2-nitrophenoxyphenyl, 3-nitrophenoxyphenyl, 2-methylphenoxyphenyl, 4-methylphenoxyphenyl, 3-trifluoromethylphenoxyphenyl, 2-methoxyphenoxyphenyl, 4-methoxyphenoxyphenyl, etc. Representative of the aralkyloxyphenyl groups substituted with halogen, nitro, lower alkyl, lower alkoxy or haloalkyl are 2-chlorobenzyloxyphenyl, 4-chlorobenzyloxyphenyl, 2-nitrobenzyloxyphenyl, 4-methylbenzyloxyphenyl, 2-methylbenzyloxyphenyl, 4-methoxybenzyloxyphenyl, 3-trifluoromethylbenzyloxyphenyl, 2-chlorophenethyloxyphenyl, 3-nitrophenethyloxyphenyl, 4-methylphenethyloxyphenyl, 4-methoxyphenethyloxyphenyl, 3-trifluoromethylphenethyloxyphenyl, etc.

The compounds [I] of the present invention can be prepared by various processes. Preferred examples of the process are carried out according to the following reaction equation.

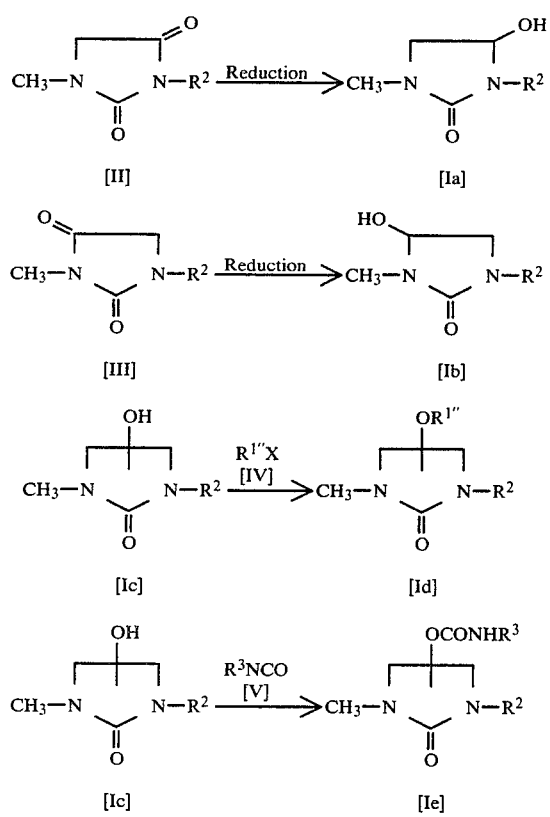

(In the reaction equations, $R^{1''}$ represents a lower alkyl group, lower alkoxy lower alkyl group, benzyl group or lower alkoxycarbonyl lower alkyl group, X represents a halogen atom, $R^3$ represents a lower alkyl group and $R^2$ is as defined above.)

The hydantoin derivatives represented by the formula [II] or [III] which are used as the starting material in the foregoing reaction equations are compounds known heretofore. For example, the hydantoin derivatives of the formula [II] or [III] wherein $R^2$ is a group-CONH—Ar can be prepared from 1-methylhydantoin or 3-methylhydantoin and allyl isocyanate by the conventional method. The reaction between the 1-methylhydantoin and allyl isocyanate and the reaction between the 3-methylhydantoin and allyl isocyanate are conducted under the same conditions with or without a solvent. Useful solvents can be any of suitable solvents which do not adversely affect the reaction, such as toluene, xylene, chlorobenzene and like aromatic solvents. The ratio between the 1- or 3-methylhydantoin and the allyl isocyanate is not particularly limited and can be suitably determined over a wide range. The amount of the latter is usually about 1 to about 10 moles, preferably about 1 to about 3 moles, per mole of the former. While the reaction temperature is not particularly limitative, the reaction adequately proceeds at about 100° to about 200° C. and is completed usually in about 3 to about 5 hours.

The reaction for reducing the compound [II] to the compound [Ia] and the reaction for reducing the compound [III] to the compound [Ib] can be effected in an adequate solvent. Suitable examples of the solvent are water, methyl alcohol, ethyl alcohol, propyl alcohol, butyl alcohol, and like alcohols; and a mixture of at least one of such alcohols and at least one of diethyl ether, dibutyl ether, tetrahydrofuran, dioxane and like ethers. The reducing agents which can be used in the reaction for reducing the compound [II] or [III] to the compound [Ia] or [Ib] include, for example, sodium borohydride. The ratio between the compound [II] or [III] and the sodium borohydride is not particularly limited and can be determined over a wide range. The latter is used in an amount of usually about 0.1 to about 5 moles, preferably about 0.25 to about 1 mole, per mole of the former. While the reaction temperature is not particularly limited, the reation favorably proceeds at usually about −50° to about 100° C., preferably about 0° to about 50° C. and is completed in usually about 1 to about 5 hours.

The reaction between the compound [Ic] and the alkyl halide [IV] can be conducted in the absence of a solvent or in the presence of a suitable solvent. The alkyl halides [IV] are compounds heretofore known. Adequate examples of the solvent are water, methyl alcohol, ethyl alcohol, propyl alcohol, butyl alcohol and like alcohols; diethyl ether, dipropyl ether, dibutyl ether, tetrahydrofuran, dioxane and like ethers; methylene chloride, chloroform and like halogenated hydrocarbons; benzene, toluene, xylene, chlorobenzene, nitrobenzene, and like aromatic solvents; pyridine; ethyl acetate; acetonitrile; dimethylformamide; etc. The ratio between the compound [Ic] and the compound [IV] is not particularly limited and can be selected from a broad range. The latter is used in an amount of usually about 1 to about 5 moles, preferably about 1 to about 2 moles, per mole of the former. The reaction of the compound [Ic] with the compound [IV] involves the use of a base for collecting the hydrogen halide produced as a by-product. Useful bases include, for example, sodium hydroxide, potassium hydroxide, sodium carbonate, potassium carbonate, triethylamine, tributylamine and like tertiary amines; pyridine; picoline, lutidine and like pyridines; sodium metal; sodium hydride; sodium alkoxides; etc. The ratio between the compound [Ic] and the agent for collecting the hydrogen halide is not particularly limited and can be selected from a wide range. The latter is employed in an amount of usually about 1 to about 5 moles, preferably about 1 to about 2 moles, per mole of the former. Although the reaction temperature is not particularly limited, the reaction favorably proceeds at usually about 0° to about 100° C. and is completed usually in about 5 to about 10 hours.

The reaction between the compound [Ic] and the isocyanate compound [V] is carried out in the absence or presence of a solvent. The isocyanates [V] are compounds heretofore known. Suitable examples of the isocyanate are methyl isocyanate, ethyl isocyanate, n-propyl isocyanate, isopropyl isocyanate, n-butyl isocyanate, isobutyl isocyanate, sec-butyl isocyanate, etc. The reaction without a solvent is conducted desirably in an autoclave under increased pressure to prevent the vaporization of the compound [V]. Solvents useful in the reaction can be any of suitable solvents which do not adversely affect the reaction, such as diethyl ether, dipropyl ether, dibutyl ether, tetrahydrofuran, dioxane and like ethers; methylene chloride, chloroform and like halogenated hydrocarbons; benzene, toluene, xylene, chlorobenzene and like aromatic solvents; pyridine; acetonitrile; N,N-dimethylformamide; etc. The ratio between the compound [Ic] and the compound [V] is not particularly limited and can be determined over a wide range. The latter is used in an amount of usually about 1 to about 5 moles, preferably about 1 to about 2 moles, per mole of the former.

While the use of a catalyst is optional in carrying out the reaction between the compound [Ic] and the compound [V] in the absence of a solvent, it is preferred to use a catalyst in conducting the reaction in a solvent. Useful catalysts include, for example, tertiary amines such as triethylamine, tributylamine, N,N-dimethylaniline, hexamethylenetetramine, etc. The catalyst is used in the usual amount, for example, generally in an amount of about 0.01 to about 0.5 mole per mole of the compound [Ic]. The reaction temperature is not particularly limited, but favorably proceeds at usually about 0° to about 150° C. and is completed in generally about 3 to about 15 hours.

The compound [I] of the present invention thus obtained is easily purified by the usual method such as recrystallization, solvent extraction, column chromatography or the like.

Examples of the present compounds which can be prepared by the foregoing methods are:

1-methyl-3-phenyl-4-hydroxyimidazolidine-2-one;
1-methyl-3-(2-chlorophenyl)-4-hydroxyimidazolidine-2-one;
1-methyl-3-(3,4-dichlorophenyl)-4-hydroxyimidazolidine-2-one;
1-methyl-3-(3-methylphenyl)-4-hydroxyimidazolidine-2-one;
1-methyl-3-(4-methoxyphenyl)-4-hydroxyimidazolidine-2-one;
1-methyl-3-(4-benzyloxyphenyl)-4-hydroxyimidazolidine-2-one;
1-methyl-3-(4-phenoxyphenyl)-4-hydroxyimidazolidine-2-one;
1-methyl-3-(3,4-dichlrophenyl)-4-methoxyimidazoline-2-one;
1-methyl-3-(3,4-dichlorophenyl)-4-benzyloxyimidazolidine-2-one;
1-methyl-3-(3,4-dichlorophenyl)-4-ethoxycarbonylmethyloxyimidazolidine-2-one;
1-methyl-3-(3,4-dichlorophenyl)-4-methoxymethyloxyimidazolidine-2-one;
3-methyl-4-hydroxyimidazolidine-2-one-1-carboxyanilide;
3-methyl-5-hydroxyimidazolidine-2-one-1-carboxyanilide;
3-methyl-4-hydroxyimidazolidine-2-one-1-carboxy-(2'-chloroanilide);
3-methyl-5-hydroxyimidazolidine-2-one-1-carboxy-2'-chloroanilide);
3-methyl-4-hydroxyimidazolidine-2-one-1-carboxy-(3'-chloroanilide);
3-methyl-5-hydroxyimidazolidine-2-one-1-carboxy-(3'-chloroanilide);
3-methyl-5-hydroxyimidazolidine-2-one-1-carboxy-(2',4'-dichloroanilide);
3-methyl-4-hydroxyimidazolidine-2-one-1-carboxy-(3'-methylanilide);
3-methyl-5-hydroxyimidazolidine-2-one-1-carboxy-(3'-methylanilide);
3-methyl-5-hydroxyimidazolidine-2-one-1-carboxy-(2'-methoxyanilide);
3-methyl-5-hydroxyimidazolidine-2-one-1-carboxy-(3'-trifluoromethylanilide);
3-methyl-5-hydroxyimidazolidine-2-one-1-carboxy-(3'-nitroanilide);
3-methyl-4-methoxyimidazolidine-2-one-1-carboxyanilide;
3-methyl-5-ethoxyimidazolidine-2-one-1-carboxyanilide;
3-methyl-5-methoxyimidazolidine-2-one-1-carboxy-(2'-chloroanilide);
3-methyl-5-ethoxycarbonylmethylimidazolidine-2-one-1-carboxyanilide;
3-methyl-5-methoxymethoxyimidazolidine-2-one-1-carboxyanilide;
3-methyl-4-methylcarbamoyloxyimidazolidine-2-one-1-carboxylanilide;
3-methyl-4-ethylcarbamoyloxyimidazolidine-2-one-1-carboxyanilide;
3-methyl-4-isopropylcarbamoyloxyimidazolidine-2-one-1-carboxyanilide;
2',3-dimethyl-4-methylcarbamoyloxyimidazolidine-2-one-1-carboxyanilide;
3,3'-dimethyl-4-methylcarbamoyloxyimidazolidine-2-one-1-carboxyanilide;
2'-chloro-3-methyl-4-methylcarbamoyloxyimidazolidine-2-one-1-carboxyanilide;
2'-chloro-3-methyl-4-isopropylcarbamoyloxyimidazolidine-2-one-1-carboxyanilide;
2',4'-dichloro-3-methyl-4-methylcarbamoyloxyimidazlidine-2-one-1-carboxyanilide;
3'-chloro-3-methyl-4-methylcarbamoyloxyimidazolidine-2-one-1-carboxyanilide;
3-methyl-4'-methoxy-4-methylcarbamoyloxyimidazolidine-2-one-1-carboxyanilide;
3-methyl-4'-trifluoromethyl-4-methylcarbamoyloxyimidazolidine-2-one-1-carboxyanilide; and
3-methyl-4'-benzyloxy-4-methylcarbamoyloxyimidazolidine-2-one-1-carboxyanilide.

This invention also relates to herbicides containing as their active component the imidazolidine-2-one derivative (I).

The compounds of the present invention are markedly effective in controlling weeds such as *Eclipta prostrata, Amaranthus retroflexus, Aeschynomeme indica, Alopecurus aequalis* var. *amurensis, Polygonum Hydropiper, Artemisia princeps, Erigeron sumatrensis, Rumex japonicus, Lindernia pyxidaria, Rotela indica, Echinochloa Crus-galli, Digitaria adscendens Eleusine indica, Cyperus microiria*, etc. Therefore, the present compounds are useful in preventing or controlling weeds which are harmful to agricultural crop plants such as those of citrus, apples, soy beans, corns, mulberries, tea, paddyrice, etc. or which impair the surrounding scenic beauty.

When used as a herbicide, the compounds of the present invention can be used singly or in admixture with adjuvants commonly used in manufacture of agricultural chemicals. The herbicidal composition containing the present compound can take any of forms among which an emulsion, wettable powder and granules are suitable. Examples of useful adjuvants for achieving a stable and improved herbicidal effect are diatomaceous earth, kaolin, clay, bentonite, white carbon, talc and like extenders; polyoxyethylene alkyl ether, polyoxyethylene alkylphenyl ether, polyoxyethylene sorbitan fatty acid ester, polyoxyethylene fatty acid ester, sodium alkyl benzensulfonate, sodium lignin sulfonate, sodium alkylsulfate, sodium polyoxyethylene alkylsulfate and like nonionic or anionic surfactants; xylol, acetone, methanol, ethanol, isopropanol, dioxane, dimethylformamide, dimethyl sulfoxide, carbon tetrachloride and like organic solvents; etc.

In formulating a herbicidal composition according to the present invention, adjuvants are used in such amount that about 1 to about 90% by weight, preferably about 5 to about 70% by weight, of the active component is present in the composition. While an adequate amount of the herbicidal composition to be applied is variable with the form of the composition, application mode, application season, kind of weeds to be controlled, particularly weather conditions and soil conditions tending to affect the herbicidal effect, etc., and can be determined over a wide range, the herbicidal composition of the present invention is generally applied in an amount of about 5 to about 400 g/a, preferably about 10 to about 100 g/a, calculated as the active component.

The present invention will be described below in more detail with reference to Reference Examples, Examples, Preparation Examples and Test Examples. The numbers of test compounds used in Test Examples correspond to the numbers of Examples.

REFERENCE EXAMPLE 1

Preparation of 3-methylimidazolidine-2,4-dione-1-carboxyanilide

A 5.7 g (0.05 mole) quantity of 3-methylhydantion and 5.9 g of phenyl isocyanate were dissolved in each other in an oil bath at 150° C. for 3 hours. The solution was recrystallized from dimethylformamide, giving 9.0 g of colorless crystals in 78% yield.

M.P.: 219° to 220° C.

The NMR data of the crystals analyzed in DMSO-$d_6$ were as follows.

δ 3.00 ppm (3H), δ 4.33 ppm (2H).
δ 7.00 ppm (5H).

| Elementary analysis (for $C_{11}H_{11}N_3O_3$) | | | |
|---|---|---|---|
| | C | H | N |
| Found (%) | 56.90 | 4.75 | 18.10 |
| Calcd. (%) | 56.89 | 4.77 | 18.09 |

The result thus obtained confirmed that the product thus prepared was a compound of the formula

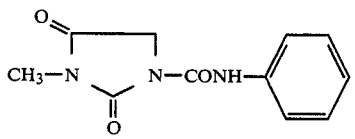

REFERENCE EXAMPLE 2

Preparation of 3-methylimidazolidine-2,5-dione-1-carboxyanilide

A 5.7 g (0.05 mole) quantity of 1-methylhydantoin and 5.9 g (0.05 mole) of phenyl isocyanate underwent dissolution in an oil bath at 180° C. for 3 hours. The solution was washed well with water and recrystallized from ethanol, giving 3.7 g of colorless crystals in 32% yield.

M.P.: 160° to 160.5° C.

The NMR data of the crystals analyzed in DMSO-$d_6$ were as follows.

δ 3.03 ppm (3H), δ 4.00 ppm (2H).
δ 7.00–7.70 ppm (5H).

| Elementary analysis (for $C_{11}H_{11}N_3O_3$) | | | |
|---|---|---|---|
| | C | H | N |
| Found (%) | 56.91 | 4.76 | 18.07 |
| Calcd. (%) | 56.89 | 4.77 | 18.09 |

The above result confirmed that the product obtained above was a compound of the formula

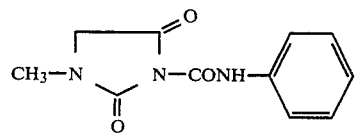

EXAMPLE 1

Preparation of 1-methyl-3-(3,4-dichlorophenyl)-4-hydroxyimidazolidine-2-one

A 10.4 g (0.04 mole) quantity of 1-methyl-3-(3,4-dichlorophenyl)hydantoin was suspended in 80 ml of methanol. The suspension was cooled to 10° C. and 1.5 g of sodium borohydride was added thereto with stirring. After the addition, the mixture was stirred for 30 minutes and warmed to room temperature, followed by further agitation for 2 hours. After completion of the reaction, the reaction mixture was concentrated and water was added to the residue to deposit crystals. The crystals were filtered and recrystallized from ethanol, affording 9.2 g of white crystals in 88% yield.

M.P.: 185° to 186° C.

The NMR data of the crystals analyzed in DMSO-$d_6$ were as follows.

δ 2.85 ppm (3H), δ 3.28 ppm (1H).
δ 3.65 ppm (1H), δ 5.57 ppm (1H).
δ 6.45 ppm (1H), δ 7.36 ppm (1H).
δ 7.68 ppm (1H), δ 7.97 ppm (1H).

| Elementary analysis (for $C_{10}H_{10}N_2O_2Cl_2$) | | | |
|---|---|---|---|
| | C | H | N |
| Found (%) | 46.04 | 3.77 | 10.69 |
| Calcd. (%) | 46.00 | 3.86 | 10.73 |

The above result confirmed that the product obtained above was a compound of the formula

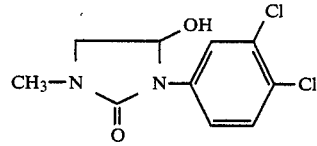

EXAMPLE 2

Preparation of 1-methyl-3-(3,4-dichlorophenyl)-4-ethoxyimidazolidine-2-one

Dissolved in 100 ml of dimethylformamide was 10.4 g (0.04 mole) of 1-methyl-3-(3,4-dichlorophenyl)-4-hydroxyimidazolidine-2-one. The solution was cooled to 10° C. and 2 g (0.04 mole) of sodium hydride was added to the solution with stirring. After the addition, the mixture was stirred for 30 minutes and 4.4 g of ethyl bromide was added dropwise. The mixture was stirred at room temperature for 2 hours and water was added to the reaction mixture. The mixture was extracted with chloroform and the chloroform extract was concentrated, giving 9.5 g of an oil in 82.1% yield.

The oil was purified by silica gel column chromatography using as a solvent a mixture of benzene and ethyl acetate (1:1).

The oil was subjected to NMR in deuteriochloroform (CDCl₃) with the following result.

δ 1.19 ppm (3H), δ 2.90 ppm (3H).
δ 3.30–3.72 ppm (4H).
δ 5.43 ppm (1H), δ 7.38 ppm (1H).
δ 7.60 ppm (1H), δ 7.90 ppm (1H).

| Elementary analysis (for $C_{12}H_{14}N_2O_2Cl_2$) | | | |
|---|---|---|---|
| | C | H | N |
| Found (%) | 49.79 | 4.81 | 9.72 |

| -continued | | | |
|---|---|---|---|
| Elementary analysis (for $C_{12}H_{14}N_2O_2Cl_2$) | | | |
| | C | H | N |
| Calcd. (%) | 49.84 | 4.88 | 9.69 |

The above result confirmed that the product obtained above was a compound of the formula

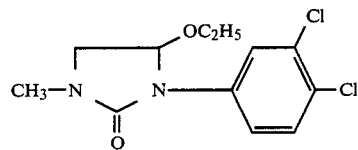

EXAMPLES 3 TO 16

The same procedure as Example 1 or 2 was repeated to produce compounds. Table 1 below shows the melting points and NMR data of the compounds thus obtained.

TABLE 1

| Ex. No. | Formula | M.P. (°C.) | NMR (δ, CDCl₃ or CDCl₃/DMSO-d₆) |
|---|---|---|---|
| 3 | CH₃—N, N-(4-Cl-C₆H₄), CH-OH, C=O | 174–175 | 2.86 (3H), 3.25 (1H) 3.67 (1H), 5.56 (1H) 6.33 (1H), 7.28 (2H) 7.63 (2H) |
| 4 | CH₃—N, N-(C₆H₄-CF₃), CH-OH, C=O | 149–150 | 2.90 (3H), 3.28 (1H) 3.70 (1H), 5.63 (1H) 6.50 (1H), 7.20–8.20 (4H) |
| 5 | CH₃—N, N-(C₆H₄-OCH₃), CH-OH, C=O | 148–149 | 2.85 (3H), 3.25 (1H) 3.63 (1H), 3.78 (3H) 5.58 (1H), 6.32 (1H) 6.65 (1H), 7.20–7.50 (3H) |
| 6 | CH₃—N, N-(4-OCH₃-C₆H₄), CH-OH, C=O | 165–167 | 2.82 (3H), 3.22 (1H) 3.60 (1H), 3.77 (3H) 5.48 (1H), 6.30 (1H) 6.88 (2H), 7.52 (2H) |
| 7 | CH₃—N, N-(C₆H₄-CH₃), CH-OH, C=O | 104–105 | 2.30 (3H), 2.60 (3H) 3.20 (1H), 3.52 (1H) 5.00 (1H), 5.41 (1H) 6.80–7.60 (4H) |
| 8 | CH₃—N, N-C₆H₅, CH-OH, C=O | 173–174 | 2.86 (3H), 3.25 (1H) 3.65 (1H), 5.60 (1H) 6.25 (1H), 7.0–7.80 (5H) |

TABLE 1-continued

| Ex. No. | Formula | M.P. (°C.) | NMR (δ, CDCl₃ or CDCl₃/DMSO-d₆) |
|---|---|---|---|
| 9 | CH₃—N(C=O)N—(OH)CH₂— with N-phenyl-OCH₂CH₂-phenyl | 130–132 | 2.65 (3H), 3.05 (2H) 3.20 (1H), 3.55 (1H) 4.17 (2H), 4.95 (1H) 5.50 (1H), 6.95 (2H) 7.20–7.50 (7H) |
| 10 | CH₃—N(C=O)N—(OH)CH— with N-phenyl-OCH₂-phenyl | 162–163 | 2.60 (3H), 3.17 (1H) 3.53 (1H), 4.65 (1H) 5.02 (2H), 5.40 (1H) 6.93 (2H), 7.40 (5H) 7.55 (2H) |
| 11 | CH₃—N(C=O)N—(OH)CH— with N-phenyl-O-phenyl | 188–190 | 2.90 (3H), 3.30 (1H) 3.68 (1H), 5.60 (1H) 6.32 (1H), 6.90– 7.80 (9H) |
| 12 | CH₃—N(C=O)N—(OH)CH— with N-phenyl-O-(4-Cl-phenyl) | 150–151 | 2.68 (3H), 3.25 (1H) 3.60 (1H), 4.90 (1H) 5.50 (1H), 6.95 (4H) 7.32 (2H), 7.67 (2H) |
| 13 | CH₃—N(C=O)N—(OCH₃)CH— with N-(3,4-dichlorophenyl) | 133–134 | 2.90 (3H), 3.23 (3H) 3.50 (2H), 5.47 (1H) 7.40 (1H), 7.60 (1H) 7.90 (1H) |
| 14 | CH₃—N(C=O)N—(OCH₂OCH₃)CH— with N-(3,4-dichlorophenyl) | 86–87 | 2.90 (3H), 3.35 (3H) 3.60 (2H), 4.72 (2H) 5.60 (1H), 7.40 (1H) 7.60 (1H), 7.80 (1H) |
| 15 | CH₃—N(C=O)N—(OCH₂-phenyl)CH— with N-(3,4-dichlorophenyl) | 101–102 | 2.90 (3H), 3.50 (2H) 4.47 (2H), 5.57 (1H) 7.30–7.70 (7H) 7.88 (1H) |
| 16 | CH₃—N(C=O)N—(OCH₂COOC₂H₅)CH— with N-(3,4-dichlorophenyl) | 91–92 | 1.25 (3H), 2.90 (3H) 3.60 (2H), 4.08 (2H) 4.20 (2H), 5.65 (1H) 7.40 (1H), 7.63 (1H) 7.93 (1H) |

EXAMPLE 17

Preparation of 3-methyl-4-hydroxyimidazolidine-2-one-1-carboxyanilide

A 7.0 g (0.03 mole) quantity of 3-methylimidazolidine-2,4-dione-1-carboxyanilide was suspended in 50 ml of methanol. The suspension was cooled to 10° C. and 1.2 g of sodium borohydride was added with stirring. The mixture was stirred for 30 minutes and warmed to room temperature, followed by further agitation for 10 hours. After completion of the reaction, the reaction mixture was concentrated and water was added to the residue to deposit crystals. The crystals were filtered and recrystallized from ethanol, giving 5.4 g of colorless crystals in 76% yield.

M.P.: 156° to 157° C.

The NMR data of the crystals analyzed in deuteriochloroform were as follows.

δ 2.70 ppm (3H), δ 3.85 ppm (2H).
δ 5.00 ppm (1H), δ 7.00–7.70 ppm (5H).

| Elementary analysis (for C₁₁H₁₃N₃O₃) | | | |
|---|---|---|---|
| | C | H | N |
| Found (%) | 56.13 | 5.59 | 17.87 |
| Calcd. (%) | 56.16 | 5.57 | 17.86 |

The above result confirmed that the product obtained above was a compound of the formula

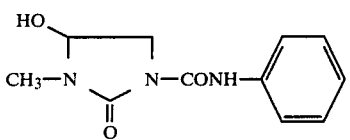

EXAMPLE 18

The NMR data of the product analyzed in deuteriochloroform were as follows.
δ 2.90 ppm (3H), δ 3.30 ppm (1H).
δ 3.65 ppm (1H), δ 4.47 ppm (1H).
δ 6.00 ppm (1H), δ 7.10–7.70 ppm (5H).

| Elementary analysis (for $C_{11}H_{13}N_3O_3$) | | | |
|---|---|---|---|
| | C | H | N |
| Found (%) | 56.18 | 5.54 | 17.89 |
| Calcd. (%) | 56.16 | 5.57 | 17.86 |

The above result confirmed that the product obtained above was a compound of the formula

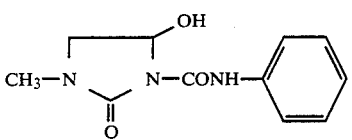

EXAMPLE 19

Preparation of 3-methyl-5-methoxyimidazolidine-2-one-1-carboxy-(3-methylanilide)

A 2.5 g (0.01 mole) of 3-methyl-5-hydroxyimidazolidine-2-one-1-carboxy-(3-methylanilide) was dissolved in 40 ml of dimethylformamide. The solution was cooled to 10° C. and 0.5 g (0.01 mole) of sodium hydride was added to the solution with stirring. The mixture was stirred for 30 minutes and 1.5 g (0.01 mole) of methyl iodide was added dropwise. The mixture was stirred at room temperature for 2 hours. Water was added to the reaction mixture to deposit crystals. The crystals were filtered and recrystallized from ethanol, giving 2.0 g of colorless crystals in 76% yield.
M.P.: 104° to 105° C.

The NMR data of the crystals analyzed in deuteriochloroform were as follows.
δ 2.32 ppm (3H), δ 2.90 ppm (3H).
δ 3.24 ppm (1H), δ 3.52 ppm (3H).
δ 3.60 ppm (1H), δ 5.65 ppm (1H).
δ 6.97 ppm (1H), δ 7.20–7.50 ppm (3H).

| Elementary analysis (for $C_{13}H_{17}N_3O_3$) | | | |
|---|---|---|---|
| | C | H | N |
| Found (%) | 59.28 | 6.54 | 15.98 |
| Calcd. (%) | 59.30 | 6.51 | 15.96 |

The above result confirmed that the product thus obtained was a compound of the formula

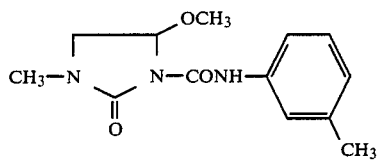

EXAMPLES 20 TO 34

Compounds were prepared in the same manner as in Examples 17 to 19. Table 2 below shows the melting points and NMR data of the compounds.

TABLE 2

| Ex. No. | Formula | M.P. (°C.) | NMR (δ, CDCl₃) |
|---|---|---|---|
| 20 | OH, CH₃—N, N—CONH—(2-Cl-phenyl), O | 179–180 | 2.88 (3H), 2.90 (2H) 2.97 (1H), 5.10 (1H) 6.95–7.50 (3H) 8.25 (1H) |
| 21 | OH, CH₃—N, N—CONH—(3-CH₃-phenyl), O | 169–170 | 2.30 (3H), 2.70 (3H) 3.80 (2H), 4.50 (1H) 4.95 (1H), 6.95 (1H) 7.25 (3H) |
| 22 | OH, CH₃—N, N—CONH—(3-Cl-phenyl), O | 168–169 | 2.93 (3H), 3.31 (1H) 3.70 (1H), 5.10 (1H) 6.00 (1H), 6.90–7.65 (3H), 8.45 (1H) |

TABLE 2-continued

| Ex. No. | Formula | M.P. (°C.) | NMR (δ, CDCl₃) |
|---|---|---|---|
| 23 | CH₃—N(—OH)—N—CONH—(3-Cl-C₆H₄), ring with C=O | 160.5–161 | 2.93 (3H), 3.30 (1H) 3.44 (1H), 4.35 (1H) 6.00 (1H), 7.05– 7.50 (3H), 7.72 (1H) |
| 24 | CH₃—N(—OH)—N—CONH—(3,4-Cl₂-C₆H₃), ring with C=O | 201–201.5 | 2.90 (3H), 3.27 (1H) 3.70 (1H), 5.90 (1H) 6.45 (1H), 7.40 (2H) 7.90 (1H) |
| 25 | CH₃—N(—OH)—N—CONH—(2-Br-C₆H₄), ring with C=O | 148–149 | 2.92 (3H), 3.30 (1H) 3.65 (1H), 4.70 (1H) 6.00 (1H), 6.90– 7.70 (3H), 8.30 (1H) |
| 26 | CH₃—N(—OH)—N—CONH—(2-CH₃-C₆H₄), ring with C=O | 173–174 | 2.32 (3H), 2.90 (3H) 3.30 (1H), 3.65 (1H) 4.47 (1H), 6.00 (1H) 7.05–7.45 (3H) 8.05 (1H) |
| 27 | CH₃—N(—OH)—N—CONH—(3-CH₃-C₆H₄), ring with C=O | 164–164.5 | 2.32 (3H), 2.90 (3H) 3.27 (1H), 3.60 (1H) 4.63 (1H), 6.00 (1H) 7.00 (1H), 7.35 (3H) |
| 28 | CH₃—N(—OH)—N—CONH—(4-CH₃-C₆H₄), ring with C=O | 196–197 | 2.30 (3H), 2.90 (3H) 3.23 (1H), 3.60 (1H) 6.95 (2H), 7.12 (2H) 7.45 (2H) |
| 29 | CH₃—N(—OH)—N—CONH—(2-OCH₃-C₆H₄), ring with C=O | 174–175 | 2.85 (3H), 3.20 (1H) 3.55 (1H), 3.82 (3H) 4.50 (1H), 5.85 (1H) 6.80–7.10 (3H) 8.10 (1H) |
| 30 | CH₃—N(—OH)—N—CONH—(4-OCH₃-C₆H₄), ring with C=O | 154–155 | 2.90 (3H), 3.26 (1H) 3.60 (1H), 3.80 (3H) 4.63 (1H), 5.96 (1H) 6.70 (1H), 7.05– 7.40 (3H) |
| 31 | CH₃—N(—OCH₂OCH₃)—N—CONH—(3-CH₃-C₆H₄), ring with C=O | 75–76 | 2.31 (3H), 2.90 (3H) 2.30 (1H), 2.40 (3H) 3.61 (1H), 4.68 (1H) 5.18 (1H), 5.82 (1H) 6.80–7.50 (1H) |

TABLE 2-continued

| Ex. No. | Formula | M.P. (°C.) | NMR (δ, CDCl₃) |
|---|---|---|---|
| 32 | CH₃—N(C=O)N—CONH—C₆H₄—CH₃ with OCH₂CO₂C₂H₅ substituent | 127–128 | 1.25 (3H), 2.32 (3H) 2.91 (3H), 3.65 (2H) 4.21 (2H), 4.56 (2H) 5.77 (1H), 6.90– 7.50 (4H) |
| 33 | CH₃—N(C=O)N—CONH—C₆H₄—NO₂ with OH substituent | 162–164 | 2.86 (3H), 3.34 (1H) 3.70 (1H), 5.15 (1H) 6.00 (1H), 6.5– 7.5 (4H) |
| 34 | CH₃—N(C=O)N—CONH—C₆H₄—CF₃ with OH substituent | 146–148 | 2.90 (3H), 3.20 (1H) 3.64 (1H), 4.63 (1H) 5.85 (1H), 6.9– 7.5 (4H) |

EXAMPLE 35

Preparation of 3.3′-dimethyl-4-hydroxyimidazolidine-2-one-1-carboxyanilide

A 7.4 g (0.03 mole) quantity of 3.3′-dimethylimidazolidine-2,5-dione-1-carboxyanilide was suspended in 50 ml of methanol. The suspension was cooled to 10° C. and 1.2 g (0.03 mole) of sodium boron hydride was added with stirring. The mixture was agitated for 30 minutes and was warmed to room temperature, followed by further agitation for 2 hours. After completion of the reaction, the reaction mixture was concentrated and water was added to the residue to deposit crystals. The crystals were filtered and recrystallized from ethanol, giving 6.7 g of colorless crystals in 90% yield.

M.P.: 164° to 164.5° C.

EXAMPLE 36

Preparation of 3.3′-dimethyl-4-methylcarbamoyloxyimidazolidine-2-one-1-carboxyanilide Dissolved in 50 ml of chloroform was 5.0 g (0.02 mole) of 3.3′-dimethyl-4-hydroxyimidazolidine-2-one-1-carboxyanilide. Triethylamine (0.5 ml) was added to the solution. The mixture was cooled to 5° C. and 1.7 g (0.03 mole) of methyl isocyanate was added dropwise with stirring. Further stirring continued for 30 minutes and the reaction mixture was warmed to room temperature, followed by 5 hours of agitation. After completion of the reaction, the reaction mixture was concentrated under reduced pressure to afford a crystalline residue. The residue was recrystallized from ethanol, giving 5.2 g of colorless crystals in 85% yield.

M.P.: 130° to 131° C.

The NMR data of the crystals analyzed in deuteriochloroform were as follows.

δ 2.30 ppm (3H), δ 2.77 ppm (3H).
δ 2.80 ppm (3H), δ 3.30 ppm (1H).
δ 5.17 ppm (1H), δ 6.75 ppm (1H).
δ 6.80–7.50 ppm (4H).

| Elementary analysis (for C₁₄H₁₈N₄O₄ = 306.32) | | | |
|---|---|---|---|
| | C | H | N |
| Found (%) | 54.85 | 5.93 | 18.31 |
| Calcd. (%) | 54.89 | 5.92 | 18.29 |

The above result confirmed that the product obtained above was a compound of the formula

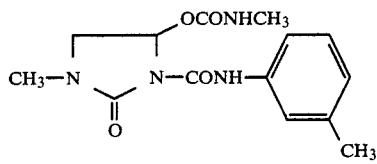

EXAMPLE 37

Preparation of 4′-chloro-3-methyl-4-ethylcarbamoyloxyimidazolidine-2-one-1-carboxyanilide Dissolved in 40 ml of chloroform was 2.7 g (0.01 mole) of 4′-chloro-3-methyl-4-hydroxyimidazolidine-2-one-1-carboxyanilide. To the solution was added 0.4 ml of triethylamine. The mixture was cooled to 5° C. and 1.1 g (0.015 mole) of ethyl isocyanate was added dropwise with stirring. Further agitation followed for 30 minutes and the reaction mixture was warmed to room temperature, followed by 12 hours of agitation. After completion of the reaction, the reaction mixture was concentrated under reduced pressure to afford a crystalline residue. The residue was recrystallized from ethanol, giving 2.6 g of colorless crystals in 77% yield.

M.P.: 156° to 157° C.

The NMR data of the crystals analyzed in deuteriochloroform were as follows.

δ 1.12 ppm (3H), δ 2.82 ppm (3H).
δ 3.10–3.50 ppm (3H).
δ 3.70 ppm (1H), δ 5.20 ppm (1H).
δ 6.70 ppm (1H), δ 7.28 ppm (2H).
7.53 ppm (2H).

| Elementary analysis (for $C_{14}H_{17}N_4O_4Cl$ = 340.77) | | | |
|---|---|---|---|
| | C | H | N |
| Found (%) | 49.30 | 5.05 | 16.45 |
| Calcd. (%) | 49.35 | 5.03 | 16.44 |

The above result confirmed that the product obtained above was a compound of the formula

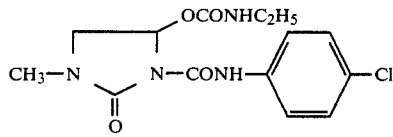

EXAMPLES 38 TO 52

The same procedure as Example 36 or 37 was repeated to produce compounds. Table 3 below shows the melting points and NMR data of the compounds obtained.

TABLE 3

| Ex. No. | Formula | M.P. (°C.) | NMR ($\delta$, $CDCl_3$) |
|---|---|---|---|
| 38 | $CH_3-N$, $NCONH-$phenyl, $OCONHCH_3$ | 150–151 | 2.82 (3H), 2.85 (3H) 3.35 (1H), 3.72 (1H) 5.20 (1H), 6.78 (1H) 7.10–7.70 (5H) |
| 39 | $CH_3-N$, $NCONH-$(2-Cl-phenyl), $OCONHCH_3$ | 163–164 | 2.76 (3H), 2.85 (3H) 3.30 (1H), 3.70 (1H) 5.20 (1H), 6.63 (1H) 6.81–7.40 (3H) 8.20 (1H) |
| 40 | $CH_3-N$, $NCONH-$(4-Cl-phenyl), $OCONHCH_3$ | 184–185 | 2.79 (3H), 2.83 (3H) 3.30 (1H), 3.72 (1H) 5.15 (1H), 6.73 (1H) 7.29 (2H), 7.55 (2H) |
| 41 | $CH_3-N$, $NCONH-$(2-CH$_3$-phenyl), $OCONHCH_3$ | 164–165 | 2.33 (3H), 2.63 (3H) 2.78 (3H), 3.22 (1H) 3.65 (1H), 5.60 (1H) 6.75 (1H), 7.00– 7.30 (3H), 8.12 (1H) |
| 42 | $CH_3-N$, $NCONH-$(3-CF$_3$-phenyl), $OCONHCH_3$ | 172–173 | 2.80 (6H), 3.35 (1H) 3.72 (1H), 5.20 (1H) 6.75 (1H), 7.30– 7.70 (3H), 8.00 (1H) |
| 43 | $CH_3-N$, $NCONH-$(2-OCH$_2$-phenyl-phenyl), $OCONHCH_3$ | 138–139 | 2.75 (3H), 2.86 (3H) 3.35 (1H), 3.70 (1H) 5.00 (1H), 5.20 (1H) 6.75 (1H), 6.90– 7.10 (3H), 7.25– 7.60 (5H), 8.32 (1H) |
| 44 | $CH_3-N$, $NCONH-$(2-OCH(CH$_3$)$_2$-phenyl), $OCONHCH_3$ | 130–131 | 1.40 (6H), 2.82 (3H) 2.90 (3H), 3.15– 3.50 (2H), 3.72 (1H) 4.70 (1H), 6.75 (1H) 6.90–7.20 (3H) 8.30 (1H) |
| 45 | $CH_3-N$, $NCONH-$phenyl, $OCONHC_2H_5$ | 138–139 | 1.12 (3H), 2.82 (3H) 3.10–3.50 (3H) 3.70 (1H), 5.15 (1H) 6.73 (1H), 7.10– 7.70 (5H) |

TABLE 3-continued

| Ex. No. | Formula | M.P. (°C.) | NMR (δ, CDCl$_3$) |
|---|---|---|---|
| 46 | CH$_3$-N(C=O)-N(OCONHC$_2$H$_5$)-CONH-(2,5-dimethylphenyl) | 154–155 | 1.13 (3H), 2.29 (6H) 2.73 (3H), 3.05–3.45 (3H), 3.70 (1H) 5.35 (1H), 6.60–7.20 (3H), 7.97 (1H) |
| 47 | CH$_3$-N(C=O)-N(OCONHC$_2$H$_5$)-CONH-(4-OCH$_3$-phenyl) | 161–162 | 1.12 (3H), 2.80 (3H) 3.23 (2H), 3.30 (1H) 3.68 (1H), 3.79 (3H) 5.40 (1H), 6.72 (1H) 6.89 (2H), 7.49 (2H) |
| 48 | CH$_3$-N(C=O)-N(OCONH(CH$_2$)$_2$CH$_3$)-CONH-(4-Cl-phenyl) | 137–138 | 0.90 (3H), 1.45 (2H) 2.85 (3H), 3.15 (2H) 3.36 (1H), 3.72 (1H) 5.20 (1H), 6.73 (1H) 7.28 (2H), 7.55 (2H) |
| 49 | CH$_3$-N(C=O)-N(OCONH(CH$_2$)$_2$CH$_3$)-CONH-(2,5-dimethylphenyl) | 139–140 | 0.93 (3H), 1.50 (2H) 2.30 (6H), 2.80 (3H) 3.20 (2H), 3.35 (1H) 3.72 (1H), 5.28 (1H) 6.75 (1H), 6.80–7.18 (2H), 8.00 (1H) |
| 50 | CH$_3$-N(C=O)-N(OCONHCH(CH$_3$)$_2$)-CONH-phenyl | 170–171 | 1.15 (6H), 2.86 (3H) 3.45 (1H), 3.55–4.00 (2H), 4.95 (1H) 6.70 (1H), 7.10–7.70 (5H) |
| 51 | CH$_3$-N(C=O)-N(OCONHCH(CH$_3$)$_2$)-CONH-(2-CH$_3$-phenyl) | 196–197 | 1.15 (6H), 2.32 (3H) 2.78 (3H), 3.32 (1H) 3.55–3.90 (2H) 5.10 (1H), 6.70 (1H) 7.00–7.35 (3H) 8.10 (1H) |
| 52 | CH$_3$-N(C=O)-N(OCONHCH(CH$_3$)$_2$)-CONH-(3-CH$_3$-phenyl) | 156–157 | 1.15 (6H), 2.30 (3H) 2.76 (3H), 3.25 (1H) 3.50–4.00 (2H) 5.25 (1H), 6.69 (1H) 6.95 (1H), 7.15–7.50 (3H) |

| Preparation Example 1 (50% wettable powder) | Part by weight |
|---|---|
| Compound obtained in Example 1 | 50 |
| Sodium lignin sulfonate | 1 |
| Sodium dodecylbenzenesulfonate | 4 |
| Clay | 45 |

| Preparation Example 2 (30% emulsion) | Part by weight |
|---|---|
| Compound obtained in Example 2 | 30 |
| Polyoxyethylenenonyl phenyl ether | 10 |
| Dimethylformamide | 20 |
| Xylene | 40 |

| Preparation Example 3 (10% granules) | Part by weight |
|---|---|
| Compound obtained in Example 3 | 10 |
| Sodium lignin sulfonate | 0.5 |
| Sodium dodecylbenzenesulfonate | 2 |
| Diatomaceous earth | 27.5 |
| Bentonite | 60 |

The wettable powder was prepared by pulverizing a uniform admixture of the components. The emulsion was produced by dissolving a uniform admixture of the components. The granules were prepared by adding water to a uniform admixture of the components, fully kneading the mixture, granulating the resulting mass, finely dividing the granules and drying the finely divided particles.

TEST EXAMPLE 1

(test by application of the herbicide to soil)

Wagner pots each having an area of 1/2000 a were filled with sterilized alluvial soil. Then the pots were each planted with seeds of plants in Table 4 below which were subsequently covered with soil about 0.5 to about 1.0 cm deep. Wettable powders each containing as the active component the compound obtained in respective Examples were prepared according to Preparation Example 1 and applied after dilution with water in an amount of 100 g/a calculated as the active component in such manner as to uniformly wet the entire surface of soil. The herbicidal activity of each sample was observed with unaided eye and evaluated 3 weeks after the application thereof according to the criteria indicated below in which the herbicidal activity thereof is expressed in terms of an index compared with untreated plants. Table 4 below shows the results.

| Index | Herbicidal Activity |
|---|---|
| 0 | No change |
| 1 | 1–24%* |
| 2 | 25–49% |
| 3 | 50–74% |
| 4 | 75–90% |
| 5 | Completely killed |

*The percentages represent a degree of growth inhibition.

TABLE 4

| Test compound | A | B | C | D | E | F | G |
|---|---|---|---|---|---|---|---|
| 1 | 5 | 5 | 5 | 5 | 5 | 5 | 5 |
| 2 | 5 | 5 | 5 | 5 | 5 | 5 | 5 |
| 3 | 5 | 5 | 5 | 5 | 5 | 5 | 5 |
| 4 | 5 | 5 | 5 | 5 | 5 | 5 | 5 |
| 5 | 5 | 4 | 3 | 3 | 5 | 4 | 3 |
| 6 | 5 | 5 | 1 | 1 | 4 | 0 | 2 |
| 7 | 5 | 5 | 5 | 5 | 5 | 5 | 5 |
| 8 | 5 | 5 | 3 | 3 | 5 | 3 | 4 |
| 13 | 5 | 5 | 5 | 5 | 5 | 5 | 5 |
| 14 | 5 | 5 | 5 | 5 | 5 | 5 | 5 |
| 15 | 5 | 5 | 5 | 5 | 5 | 4 | 5 |
| 16 | 5 | 5 | 5 | 5 | 5 | 5 | 5 |
| 18 | 5 | 5 | 5 | 5 | 5 | 5 | 5 |
| 19 | 5 | 5 | 5 | 5 | 5 | 5 | 5 |
| 20 | 5 | 5 | 4 | 1 | 5 | 4 | 1 |
| 21 | 5 | 4 | 5 | 2 | 4 | 4 | 2 |
| 22 | 5 | 5 | 5 | 5 | 5 | 5 | 5 |
| 23 | 5 | 5 | 5 | 5 | 5 | 5 | 5 |
| 24 | 4 | 5 | 4 | 5 | 5 | 3 | 1 |
| 25 | 5 | 5 | 5 | 5 | 5 | 5 | 5 |
| 26 | 5 | 5 | 5 | 5 | 5 | 5 | 5 |
| 27 | 5 | 5 | 5 | 5 | 5 | 5 | 5 |
| 28 | 5 | 5 | 5 | 2 | 4 | 1 | 3 |
| 29 | 5 | 5 | 5 | 2 | 2 | 5 | 1 |
| 30 | 5 | 5 | 5 | 5 | 5 | 5 | 5 |
| 31 | 5 | 5 | 5 | 5 | 5 | 5 | 5 |
| 32 | 5 | 5 | 5 | 5 | 5 | 5 | 5 |
| 33 | 5 | 5 | 5 | 5 | 5 | 4 | 5 |
| 34 | 5 | 5 | 5 | 5 | 5 | 5 | 5 |
| 37 | 5 | 4 | 5 | 2 | 4 | 4 | 2 |
| 38 | 5 | 5 | 5 | 5 | 5 | 5 | 5 |
| 39 | 5 | 5 | 5 | 5 | 5 | 5 | 5 |
| 40 | 4 | 5 | 4 | 5 | 5 | 3 | 1 |
| 41 | 5 | 5 | 5 | 5 | 5 | 5 | 5 |
| 42 | 5 | 5 | 5 | 5 | 5 | 5 | 5 |
| 43 | 3 | 2 | 2 | 3 | 1 | 1 | 1 |
| 44 | 5 | 5 | 5 | 5 | 5 | 5 | 5 |
| 45 | 5 | 4 | 5 | 3 | 4 | 4 | 3 |
| 46 | 5 | 5 | 5 | 2 | 4 | 1 | 3 |
| 47 | 5 | 5 | 5 | 2 | 2 | 5 | 1 |
| 48 | 5 | 4 | 5 | 2 | 4 | 4 | 2 |
| 49 | 5 | 5 | 5 | 5 | 5 | 5 | 5 |
| 50 | 5 | 5 | 5 | 5 | 5 | 5 | 5 |

TABLE 4-continued

| Test compound | A | B | C | D | E | F | G |
|---|---|---|---|---|---|---|---|
| 51 | 5 | 5 | 5 | 5 | 5 | 5 | 5 |
| 52 | 5 | 5 | 5 | 5 | 5 | 5 | 5 |
| Control | | | | | | | |
| compound A* | 1 | 2 | 2 | 3 | 1 | 0 | 2 |
| compound B** | 0 | 0 | 0 | 0 | 0 | 0 | 0 |

*Isocarbamide [N—(2-methylpropyl)-2-oxo-1-imidazolidine-carboxyamide] of the formula

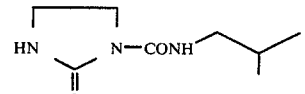

**1-Methyl-4-hydroxyimidazolidine-2-one of the formula

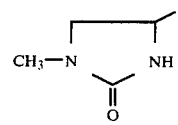

The test plants A to G shows in Table 4 were as follows.

A: *Amaranthus retroflexus*
B: *Aeschynomene indica*
C: *Echinochloa Crus-galli*
D: *Raphanus sativus*
E: *Fagopyrum esculentum*
F: *Pharbitis Nil* var. *japonica*
G: *Triticum*

TEST EXAMPLE 2

(test by application to stems and leaves)

Wagner pots each having an area of 1/2000 a were filled with sterilized alluvial soil. Then the pots were each planted with seeds of weeds shown in Table 4. When the weeds grew to a specific height (substantially to the 2 or 3 leaf stage), emulsions each containing as the active ingredient respective compounds obtained in Examples were prepared according to Preparation Example 2 and applied after dilution with water in an amount of 100 g/a calculated as the active component in such manner as to uniformly wet the entire surfaces of weed stems and leaves. The herbicidal activity of each sample was evaluated 3 weeks after the application thereof. Table 5 below shows the result. The criteria for evaluation were the same as in Test Example 1.

TABLE 5

| Test compound | A | B | C | D | E | F | G | H |
|---|---|---|---|---|---|---|---|---|
| 1 | 5 | 5 | 5 | 5 | 5 | 5 | 5 | 5 |
| 2 | 5 | 5 | 4 | 5 | 5 | 5 | 2 | 3 |
| 4 | 5 | 5 | 5 | 5 | 5 | 5 | 5 | 5 |
| 9 | 5 | 1 | 0 | 5 | 5 | 5 | 2 | 3 |
| 10 | 5 | 2 | 2 | 3 | 5 | 4 | 1 | 5 |
| 11 | 5 | 2 | 2 | 4 | 5 | 5 | 1 | 4 |
| 12 | 5 | 0 | 0 | 2 | 5 | 5 | 1 | 5 |
| 13 | 3 | 5 | 2 | 2 | 5 | 3 | 2 | 2 |
| 14 | 5 | 5 | 5 | 5 | 5 | 5 | 5 | 5 |
| 15 | 4 | 1 | 1 | 2 | 5 | 5 | 2 | 3 |
| 16 | 5 | 5 | 2 | 5 | 5 | 4 | 5 | 5 |
| 17 | 3 | 5 | 4 | 5 | 5 | 5 | 1 | 5 |
| 18 | 5 | 5 | 5 | 5 | 5 | 5 | 5 | 5 |
| 19 | 5 | 5 | 5 | 5 | 5 | 5 | 5 | 5 |
| 20 | 5 | 5 | 5 | 5 | 5 | 5 | 5 | 5 |
| 21 | 5 | 5 | 5 | 5 | 5 | 5 | 5 | 5 |
| 22 | 5 | 5 | 5 | 5 | 5 | 5 | 5 | 5 |
| 23 | 5 | 5 | 5 | 5 | 5 | 5 | 5 | 5 |
| 25 | 5 | 5 | 5 | 5 | 5 | 5 | 5 | 5 |
| 26 | 5 | 5 | 5 | 5 | 5 | 5 | 5 | 5 |

TABLE 5-continued

| Test compound | Herbicidal activity | | | | | | | |
|---|---|---|---|---|---|---|---|---|
| | A | B | C | D | E | F | G | H |
| 27 | 5 | 5 | 5 | 5 | 5 | 5 | 5 | 5 |
| 30 | 5 | 5 | 5 | 5 | 5 | 5 | 5 | 5 |
| 31 | 5 | 5 | 5 | 5 | 5 | 5 | 5 | 5 |
| 32 | 5 | 5 | 5 | 5 | 5 | 5 | 5 | 5 |
| 33 | 5 | 5 | 5 | 5 | 5 | 5 | 5 | 5 |
| 34 | 5 | 5 | 5 | 5 | 5 | 5 | 5 | 5 |
| 36 | 5 | 5 | 5 | 5 | 5 | 5 | 5 | 5 |
| 37 | 5 | 5 | 5 | 5 | 5 | 5 | 4 | 4 |
| 38 | 5 | 5 | 5 | 5 | 5 | 5 | 5 | 5 |
| 39 | 5 | 5 | 5 | 5 | 5 | 5 | 5 | 5 |
| 40 | 5 | 5 | 5 | 5 | 5 | 5 | 4 | 5 |
| 41 | 5 | 5 | 5 | 5 | 5 | 5 | 5 | 5 |
| 42 | 5 | 5 | 5 | 5 | 5 | 5 | 5 | 5 |
| 43 | 4 | 4 | 4 | 5 | 5 | 3 | 4 | 3 |
| 44 | 5 | 5 | 5 | 5 | 5 | 5 | 5 | 5 |
| 46 | 5 | 5 | 5 | 5 | 5 | 5 | 4 | 4 |
| 48 | 5 | 5 | 5 | 5 | 5 | 5 | 5 | 5 |
| 50 | 5 | 5 | 5 | 5 | 5 | 5 | 5 | 5 |
| 51 | 5 | 5 | 5 | 5 | 5 | 5 | 5 | 5 |
| 52 | 5 | 5 | 5 | 5 | 5 | 5 | 5 | 5 |
| Control compound A | 1 | 5 | 2 | 2 | 3 | 2 | 0 | 2 |
| Control compound B | 0 | 0 | 0 | 0 | 0 | 0 | 0 | 0 |

Control compounds A and B were the same as those indicated in Table 4. The test plants A to G were also the same as in Table 4. H conotes *Eclipta prostrata*.

TEST EXAMPLE 3

(test by application of the herbicide to immersed plants)

Wagner pots each having an area of 1/5000 a were filled with soil for paddy field. In the pot was placed a soil portion to provide an outer layer which portion was mixed with seeds of *Panicum crus-galli*, *Cyperus difformis*, *Lindernia Pyxilaria* and *Rotala indica*. var. *uliginosa*. The tuber of *Sagittaria pygmaea* was planted in the pot which was then supplied with water 3 cm deep. Granules were prepared according to Preparation Example 3. After planting paddy-rice plants, the herbicide samples were applied in an amount of 50 g/a calculated as the active component. Three weeks after the application of the samples, the herbicidal activity of the samples against the plants were evaluated with the result as indicated in Table 6 below. The evaluation was conducted according to the same criteria as in Test Example 1.

TABLE 6

| Test compound | Herbicidal activity | | | | | |
|---|---|---|---|---|---|---|
| | I | J | C | K | L | M |
| 1 | 5 | 5 | 5 | 5 | 3 | — |
| 2 | 5 | 5 | 5 | 5 | 3 | — |
| 3 | 5 | 5 | 3 | 2 | 0 | — |
| 4 | 5 | 5 | 5 | 4 | 3 | — |
| 5 | 4 | 3 | 5 | 1 | 3 | — |
| 6 | 4 | 4 | 5 | 3 | 0 | — |
| 7 | 3 | 3 | 5 | 4 | 1 | — |
| 8 | 4 | 3 | 5 | 1 | 0 | — |
| 9 | 3 | 5 | 5 | 5 | 1 | — |
| 12 | 3 | 5 | 5 | 5 | 3 | — |
| 13 | 5 | 5 | 5 | 5 | 4 | — |
| 14 | 5 | 5 | 5 | 5 | 5 | — |
| 15 | 5 | 5 | 5 | 5 | 3 | — |
| 16 | 5 | 5 | 5 | 4 | 3 | — |
| 18 | — | 5 | 5 | 5 | — | 5 |
| 20 | — | 5 | 5 | 5 | — | 5 |
| 24 | — | 5 | 5 | 5 | — | 5 |
| 25 | — | 5 | 5 | 5 | — | 5 |
| 27 | — | 5 | 5 | 5 | — | 5 |
| 28 | — | 5 | 5 | 5 | — | 5 |
| 29 | — | 5 | 5 | 5 | — | 5 |

TABLE 6-continued

| Test compound | Herbicidal activity | | | | | |
|---|---|---|---|---|---|---|
| | I | J | C | K | L | M |
| 34 | — | 5 | 5 | 5 | — | 5 |
| 36 | — | 5 | 5 | 5 | — | 5 |
| 38 | — | 5 | 5 | 5 | — | 5 |
| 44 | — | 5 | 5 | 5 | — | 5 |
| 50 | — | 5 | 5 | 5 | — | 5 |
| 52 | — | 5 | 5 | 5 | — | 5 |
| Control compound A | — | 3 | 3 | 2 | — | 2 |
| Control compound B | 0 | 0 | 0 | 0 | 0 | — |

The control compounds A and B were the same as those in Table 4. Test plants C and I to M were as follows.

C: *Echinochloa Grus-galli*
I: *Rotala indica*
J: *Lindernia Pyxidaria*
K: *Cyperus microiria*
L: *Sagittaria pygmaea*
M: *Cyperus difformis*

I claim:

1. An imidazolidine-2-one derivative represented by the formula

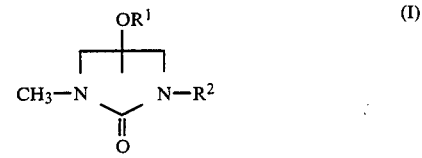

(I)

wherein R¹ represents hydrogen, lower alkyl, lower alkoxy lower alkyl, benzyl, lower alkoxycarbonyl lower alkyl or lower alkylcarbamoyloxy and R² represents —Ar or —CONH—Ar wherein Ar represents phenyl, phenoxyphenyl, benzyloxyphenyl or phenethyloxyphenyl, each of which may be substituted with a halogen atom, nitro group, lower alkyl group, lower alkoxy group or haloalkyl group of 1-3 carbons and up to 3 halogens.

2. A compound as defined in claim 1 which is represented by the formula

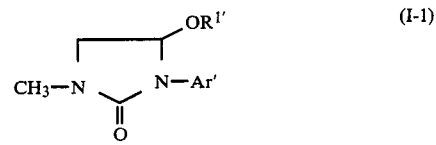

(I-1)

wherein R¹' represents hydrogen, lower alkyl, lower alkoxy lower alkyl, benzyl or lower alkoxycarbonyl lower alkyl and Ar' represents phenyl, phenoxyphenyl, benzyloxyphenyl or phenethyloxyphenyl, each of which may be substituted with a halogen atom, lower alkyl group, lower alkoxy group or haloalkyl group of 1-3 carbons and up to 3 halogens.

3. A compound as defined in claim 1 which is represented by the formula

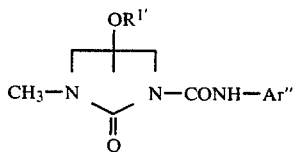
(I-2)

wherein R¹' represents a hydrogen, lower alkyl, lower alkoxy lower alkyl, benzyl or lower alkoxycarbonyl lower alkyl and Ar" represents phenyl which may be substituted with a halogen atom, nitro group, lower alkyl group, lower alkoxy group or haloalkyl group of 1-3 carbons and up to 3 halogens.

4. A compound as defined in claim 1 which is represented by the formula

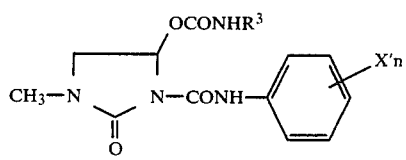
(I-3)

wherein R³ represents lower alkyl, X' represents hydrogen, halogen, lower alkyl, lower alkoxy, benzyloxy or haloalkyl of 1-3 carbons up to 3 halogens, and n is an integer of 1 to 3.

5. A herbicidal composition containing a herbicidally effective amount of an imidazolidine-2-one derivative represented by the formula

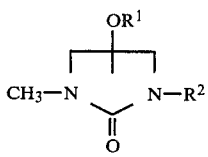
(I)

wherein R¹ represents hydrogen, lower alkyl, lower alkoxy lower alkyl, benzyl, lower alkoxycarbonyl lower alkyl or lower alkylcarbamoyloxy and R² represents —Ar or —CONH—Ar wherein Ar represents phenyl, phenoxyphenyl, benzyloxyphenyl or phenethyloxyphenyl, each of which may be substituted with a halogen atom, nitro group, lower alkyl group, lower alkoxy group or haloalkyl group of 1-3 carbons and up to 3 halogens, in combination with a carrier therefor.

6. A herbicidal composition as defined in claim 5, wherein the imidazolidine-2-one derivative is represented by the formula:

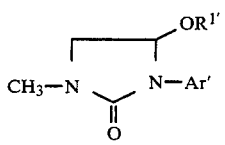
(I-1)

wherein R¹ represents hydrogen, lower alkyl, lower alkoxy lower alkyl, benzyl or lower alkoxycarbonyl lower alkyl and Ar' represents phenyl, phenoxyphenyl, benzyloxyphenyl or phenethyloxyphenyl, each of which may be substituted with a halogen atom, lower alkyl group, lower alkoxy group or haloalkyl group of 1-3 carbons and up to 3 halogens.

7. A herbicidal composition as defined in claim 5, wherein the imidazolidine-2-one derivative is represented by the formula:

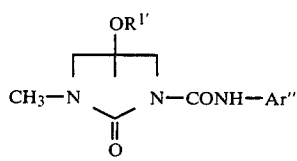
(I-2)

wherein R¹' represents a hydrogen, lower alkyl, lower alkoxy lower alkyl, benzyl or lower alkoxycarbonyl lower alkyl and Ar" represents phenyl which may be substituted with a halogen atom, nitro group, lower alkyl group, lower alkoxy group or haloalkyl group of 1-3 carbons and up to 3 halogens.

8. A herbicidal composition as defined in claim 5, wherein the imidazolidine-2-one derivative is represented by the formula:

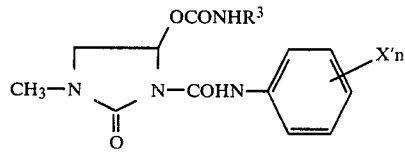
(I-3)

wherein R³ represents lower alkyl, X' represents hydrogen, halogen, lower alkyl, lower alkoxy, benzyloxy or haloalkyl of 1-3 carbons and up to 3 halogens, and n is an integer of 1 to 3.

9. A method of controlling weeds comprising applying to the weeds a herbicidally effective amount of an imidazolidine-2-one derivative represented by the formula:

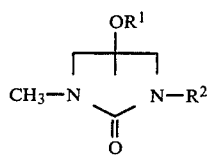
(I)

wherein R¹ represents hydrogen, lower alkyl, lower alkoxy lower alkyl, benzyl, lower alkoxycarbonyl lower alkyl or lower alkylcarbamoyloxy and R² represents —Ar or —CONH—Ar wherein Ar represents phenyl, phenoxyphenyl, benzyloxyphenyl or phenethyloxyphenyl, each of which may be substituted with a halogen atom, nitro group, lower alkyl group, lower alkoxy group or haloalkyl group of 1-3 carbons and up to 3 halogens.

10. A method of controlling weeds as defined in claim 9, wherein the imidazolidine-2-one derivative is represented by the formula:

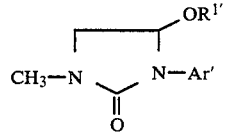
(I-1)

wherein R¹' represents hydrogen, lower alkyl, lower alkoxy lower alkyl, benzyl or lower alkoxycarbonyl lower alkyl and Ar' represents phenyl, phenoxyphenyl, benzyloxyphenyl or phenethyloxyphenyl, each of which may be substituted with a halogen atom, lower alkyl group, lower alkoxy group or haloalkyl group of 1-3 carbons and up to 3 halogens.

11. A method of controlling weeds as defined in claim 9, wherein the imidazolidine-2-one derivative is represented by the formula:

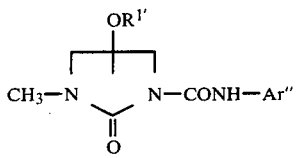
(I-2)

wherein $R^{1'}$ represents a hydrogen, lower alkyl, lower alkoxy lower alkyl, benzyl or lower alkoxycarbonyl lower alkyl and $Ar''$ represents phenyl which may be substituted with a halogen atom, nitro group, lower alkyl group, lower alkoxy group or haloalkyl group of 1-3 carbons and up to 3 halogens.

12. A method of controlling weeds as defined in claim 9, wherein the imidazolidine-2-one derivative is represented by the formula:

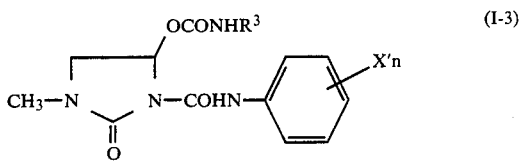
(I-3)

wherein $R^3$ represents lower alkyl, $X'$ represents hydrogen, halogen, lower alkyl, lower alkoxy, benzyloxy or haloalkyl of 1-3 carbons and up to 3 halogens, and n is an integer of 1 to 3.

* * * * *